United States Patent
Austin et al.

[11] Patent Number: 5,938,637
[45] Date of Patent: Aug. 17, 1999

[54] SINGLE-USE MEDICINE DELIVERY UNIT FOR NEEDLELESS HYPODERMIC INJECTOR

[75] Inventors: Glenn D. Austin; Timothy J. Salo; Theodore J. Colburn, all of Seattle, Wash.

[73] Assignee: Path, Seattle, Wash.

[21] Appl. No.: 08/819,563

[22] Filed: Mar. 14, 1997

[51] Int. Cl.$^6$ .................................................. A61M 5/30
[52] U.S. Cl. ........................... 604/72; 604/68; 604/141; 604/143; 604/147
[58] Field of Search ................................ 604/68, 72, 140, 604/141, 143, 147, 152, 154, 157, 257, 261, 228; 222/340, 372, 153.05, 341, 320, 575

[56] References Cited

U.S. PATENT DOCUMENTS

| | | | |
|---|---|---|---|
| 3,140,713 | 7/1964 | Ismach | 128/173 |
| 3,518,990 | 7/1970 | Banker . | |
| 4,124,024 | 11/1978 | Schwebel et al. | 128/173 H |
| 4,623,332 | 11/1986 | Lindmayer et al. | 604/68 |
| 4,626,242 | 12/1986 | Fejes et al. | 604/68 |
| 4,913,699 | 4/1990 | Parsons | 604/68 |
| 5,062,830 | 11/1991 | Dunlap . | |
| 5,190,523 | 3/1993 | Lindmayer | 604/72 |
| 5,256,142 | 10/1993 | Colvecchio . | |
| 5,312,577 | 5/1994 | Peterson et al. . | |
| 5,334,144 | 8/1994 | Alchas et al. . | |
| 5,503,627 | 4/1996 | McKinnon et al. . | |
| 5,569,189 | 10/1996 | Parsons | 604/68 |
| 5,697,917 | 12/1997 | Sadowski et al. | 604/218 |

*Primary Examiner*—Corrine McDermott
*Assistant Examiner*—Cris L. Rodriguez
*Attorney, Agent, or Firm*—Banner & Witcoff, Ltd.

[57] ABSTRACT

A disposable medicine delivery unit for use in a needleless hypodermic injector is configured to allow economical replacement, after each injection, of a patient contact surface and the entire injection flow-path of the medicament, to thereby ensure sterility with less need for repeated equipment cleaning and sterilization procedures. The delivery unit includes a piston seal configured to prevent improper reuse. The piston seal deforms and sticks in a conical end of the medicine delivery chamber at the end of its injection stroke. A push-only connection between the piston seal and a piston drive rod of the injector ensures that the latter cannot be used to retract the former. Preferably, the piston seal also includes a protruding nipple which enters and destroys the injection orifice following an injection, to further disable the delivery unit.

34 Claims, 4 Drawing Sheets

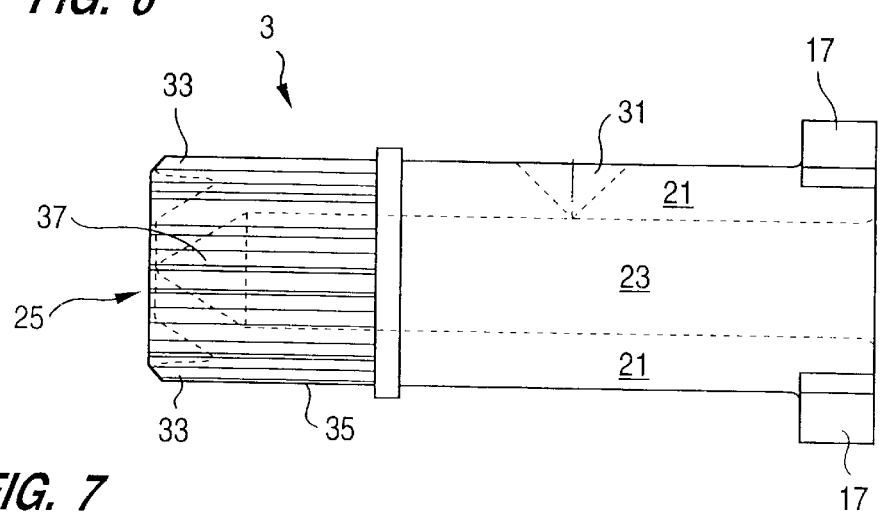
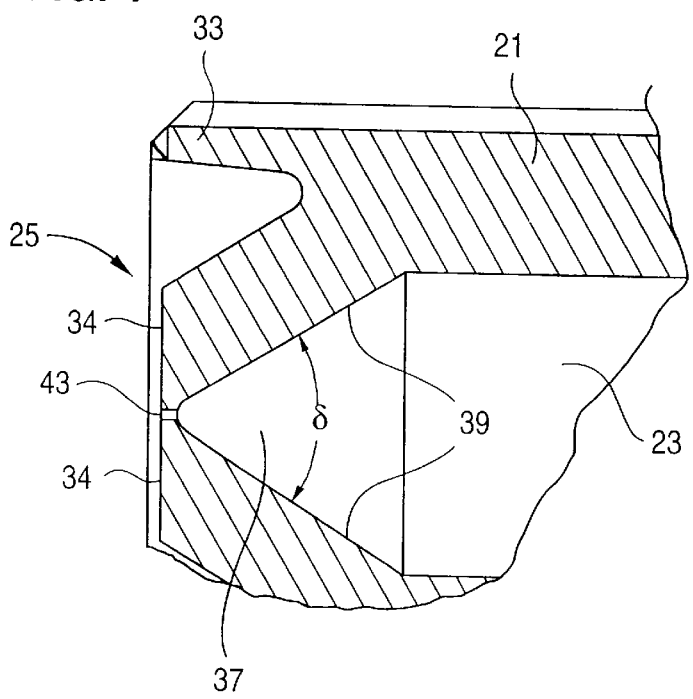
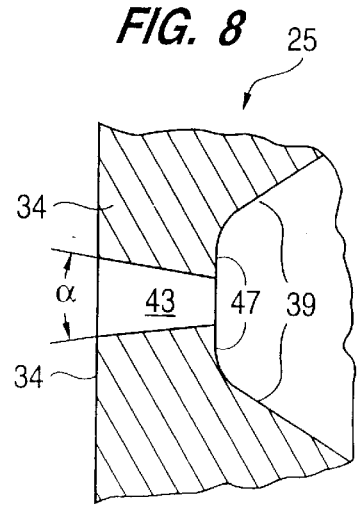
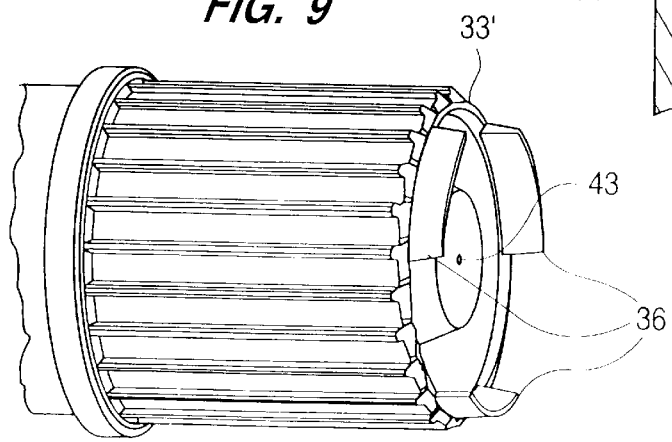

SINGLE-USE MEDICINE DELIVERY UNIT FOR NEEDLELESS HYPODERMIC INJECTOR

FEDERALLY SPONSORED RESEARCH AND DEVELOPMENT

This invention was made in part with government support under Cooperative Agreement No. HRN-5968-A-00-6007-00 awarded by the Agency for International Development. The U.S. Government has certain rights in this invention.

BACKGROUND OF THE INVENTION

The present invention relates to needleless hypodermic (subcutaneous or intramuscular) injectors, i.e., devices for delivering to a body a dose of liquid medicament by way of a fine high pressure liquid stream which penetrates the skin and deposits the medicament subcutaneously or intramuscularly. More specifically, the invention concerns single-use medicine delivery units for such devices, and means for automatically disabling the units to positively prevent unsanitary and potentially infectious reuse.

For years, health workers have administered medicine to patients using syringes and needles. (It is to be understood that "medicine" and "medicament" as used herein refers generally to any type of liquid medicament or vaccine.) However, the use of syringes and needles puts health workers and patients at risk of infection through inadvertent needle-sticks or equipment misuse. In addition, syringes and needles are difficult to disinfect or sterilize, and the use of improperly sterilized syringes and needles greatly increases the risk of blood-borne disease transmission among injection recipients. Still further, syringes and needles can cause a high level of anxiety in certain patients, and reuse of dull needles can cause extreme discomfort to the injection recipient.

Disposable syringes and needles have been used to alleviate the risk of disease transmission. However, these disposable units create hazardous waste and waste disposal problems. Inadvertent painful needle sticks and consequent spread of disease and infection may result from the handling of such medical waste. In addition, particularly in some areas of the world where disposable syringes and needles often do not reach the users in adequate quantities, the disposable units may be used more than once, contrary to their intended purpose. A further drawback to disposable needles and syringes is the high costs when the units are provided for widespread use.

Several types of needleless injectors have been developed to avoid some of the drawbacks of syringes and needles. Mass-campaign jet injectors, such as the PEDO-JET, have been used to provide fast and efficient needleless injections. However, these units are very difficult to clean or sterilize upon contamination. In addition, the mass-campaign injectors utilize a complex fluid path with dead space therein, such that a substantial amount of residual medicine is retained in the fluid path. When changing from one injectant to another, the residual fluid must be cleared to prevent unacceptable mixing of medicines. This clearing process wastes a relatively large amount of medicine before the injector is ready to inject another patient.

Personal and low-workload jet injectors, such as the VITAJET and the SICIM HYPODERMIC INJECTOR JET 2000, have also been used to provide needleless injections. The SICIM low-workload injector utilizes a complex fluid path that retains residual medicine. Accordingly, the units are difficult to sterilize, and medicine is wasted through purging when changing between medicines to be administered. On the other hand, the VITAJET personal injector fills from the front through the nozzle orifice via a removable vial adaptor. This is a slow, relatively inefficient process that, in a multi-user application, could lead to cross-contamination of the reusable fluid path components.

Commonly assigned U.S. patent application Ser. No. 08/483,192, filed Jun. 7, 1995 (hereby incorporated by reference in its entirety), discloses an air-powered needleless hypodermic injector (hereinafter "APNHI") representing a significant improvement over previous designs in several respects. In particular, the injector includes a reusable (primarily stainless steel) medicine delivery unit. The delivery unit mounts in the front end of a main injector housing and is easily removed from the main injector housing for cleaning and/or sterilization, without the need for disassembly of the delivery unit.

A medicine chamber of the APNHI medicine delivery unit receives medicine from a medicine filling mechanism (including a medicine vial) through a unique side-loading fill port. A discharge piston is slidably mounted in the chamber and has a rear rod extension which engages with an air piston driven by a relatively low-pressure air source. During an injection, the air piston drives the discharge piston forward to force medicine in the chamber through an injection nozzle located at the distal end of the chamber, to form a high pressure injection stream. The design provides a simple, removable fluid path with essentially no dead space, and thereby allows medicines to be changed without purging waste. The provision of a side-loading fill port avoids cumbersome arrangements for filling the medicine delivery chamber through the front injection orifice, and the associated increased possibility of surface contamination, as exists in many other devices. In addition, since the side-loading fill port is located very close to the piston head when the piston is in its retracted position, the fill port is closed at the beginning of the piston's discharge stroke. Such positioning of the fill port eliminates the requirement (present in the rear-loading arrangements of other devices) of check-valves to prevent medicine from flowing out of the fill port during the discharge stroke. Such check valves increase costs, are very difficult to clean, and are subject to malfunction and leakage due to their repeated exposures to the extremely high injection pressures (e.g., 3000 psi) generated within the chamber.

In certain settings, such as mass immunization campaigns conducted away from health care facilities, it may be inconvenient or impractical to frequently perform cleanings and sterilization of injector components, e.g., the medicine delivery unit of the APNHI. In such settings, it would be highly desirable to be able to employ a low cost disposable medicine delivery unit that would reduce the need for equipment sterilizations. In order to prevent improper reuse of the disposable medicine delivery units, it would also be highly desirable to provide an effective low-cost disabling function.

Alchas et al. U.S. Pat. No. 5,334,144 discloses a single use disposable needleless injector. Since the entire device (including a spring mechanism and associated trigger for driving the injector piston) is disposed of after a single use, the cost per injection is relatively high.

Colavecchio U.S. Pat. No. 5,256,142 discloses a needleless injector with a "one-shot cap." In this device, a cap forming the injection orifice which is pressed against the injection recipient's skin is broken by a striker mechanism which advances with the injection piston, whereby the device cannot be reused without replacing the cap. With such a small part replaced with each injection, the costs per dose may be considerably reduced in comparison to a wholly disposable injector. However, the Colavecchio device does not guarantee that the fluid path (and therefore the next shot) will remain free from contamination.

McKinnon et al. U.S. Pat. No. 5,503,627 discloses a needleless injector including an ampule which is preferably injection molded as a single part of polycarbonate. While the ampule may be provided as a pre-filled single use ampule, no mechanism is provided for positively preventing ampule reuse. Moreover, the refillable embodiments are subject to the filling and contamination difficulties described above in connection with the APNHI.

SUMMARY OF THE INVENTION

In view of the foregoing, it is a principal object of the present invention to provide a low-cost disposable medicine delivery unit for a needleless hypodermic injector that will ensure sterility of the fluid flow path and patient contact surface, with a reduced need for repeated sterilization and cleaning treatments.

It is a further object of the invention to effectively and efficiently prevent improper reuse of the disposable medicine delivery unit.

It is still another object of the invention to provide a disposable single-use medicine delivery unit which is well suited for use with an APNHI of the type described in aforementioned U.S. patent application Ser. No. 08/483,192.

These and other objects are achieved in accordance with the present invention by a disposable medicine delivery unit for a needleless hypodermic injector. The delivery unit includes a releasable lock device for detachably mounting the delivery unit to a main injector housing, and sidewalls defining an elongated medicine chamber. A discharge nozzle is connected with the sidewalls at a distal end of the chamber. A distal end region of the chamber adjacent the nozzle has a reduced cross-sectional area. A discharge piston seal is slidably mounted for axial movement within chamber from a first position adjacent a proximal end of the chamber to a second position within the distal end region of the chamber. The piston seal is configured relative to the distal end region of the chamber such that it enters the end region and is securely retained therein, with increased holding strength, at the end of its injection stroke.

In a second aspect, the invention is embodied in a needleless hypodermic injector assembly. The assembly includes a main injector housing containing a reciprocable driving member and a discharge rod attached to the driving member. The assembly further includes a disposable medicine delivery unit. The delivery unit includes a releasable lock device for detachably mounting the delivery unit to the main injector housing. Sidewalls of the unit define an elongated medicine chamber and a medicine fill port adjacent a proximal end of the chamber. The fill port is adapted to be connected to a source of liquid medicament. A discharge nozzle is connected with the sidewalls at a distal end of the chamber. A discharge piston seal is slidably mounted for axial movement within the chamber from a first proximal position adjacent the medicine fill port to a second distal position within an end region of the chamber adjacent the nozzle. The piston seal has a proximal end surface engageable in a push-only relation with a distal end of the discharge rod when the delivery unit is mounted in the main injector housing.

The above and other objects and features of the invention will be readily apparent and fully understood from the following detailed description of the preferred embodiments, taken in connection with the appended drawings.

BRIEF DESCRIPTION OF THE DRAWINGS

FIG. 6 is a side elevational view of the disposable medicine delivery unit.

FIG. 7 is a close-up partial sectional view illustrating a nozzle structure of the disposable medicine delivery unit.

FIG. 8 is a close-up partial sectional view illustrating more clearly an injection orifice of the nozzle structure.

FIG. 9 is a partial perspective view illustrating a modified disposable medicine delivery unit in accordance with the invention.

DETAILED DESCRIPTION OF THE PREFERRED EMBODIMENTS

Figure 1:
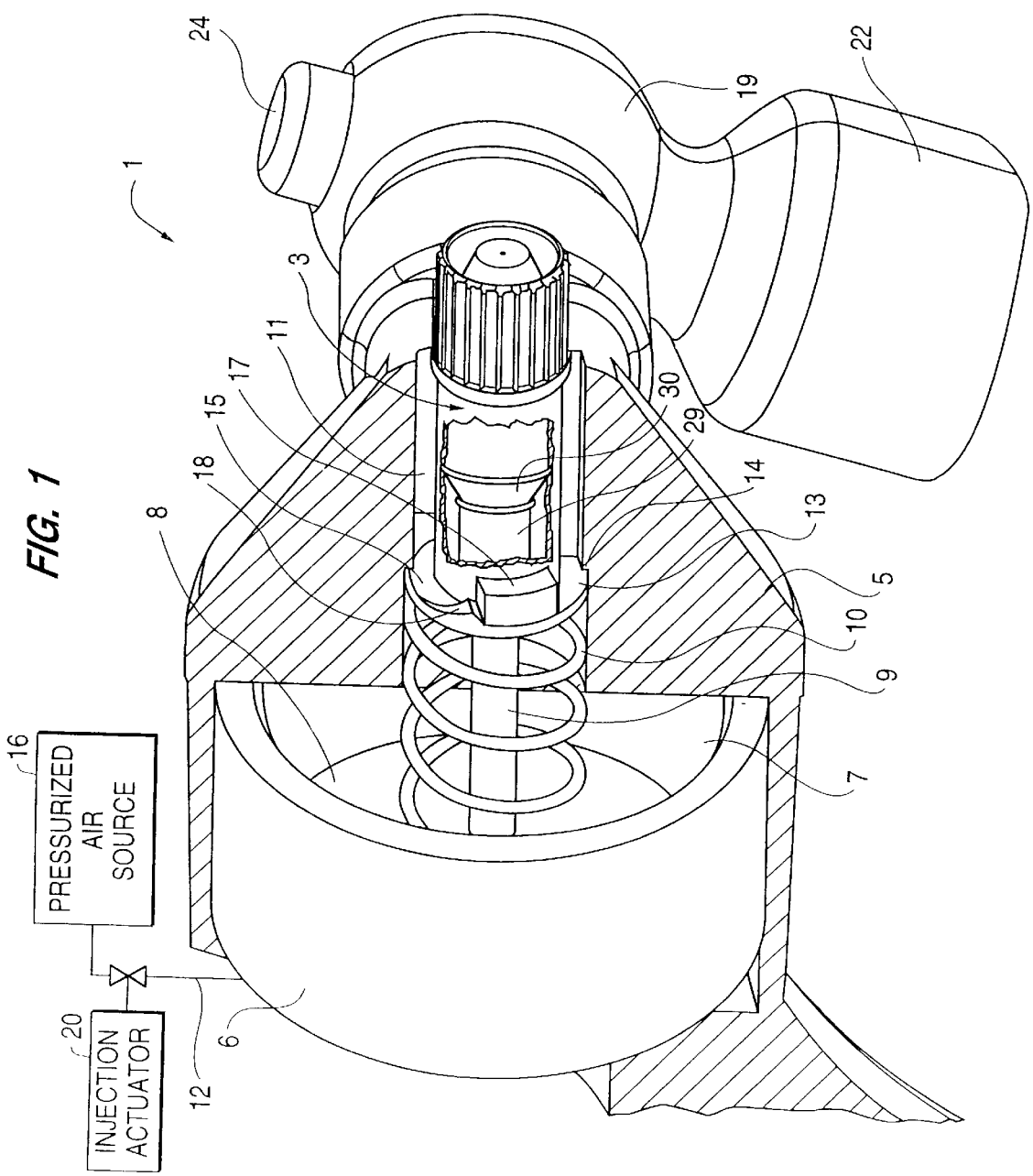
FIG. 1 is a diagrammatic partially sectioned and partially broken-away perspective view of a needleless hypodermic injector assembly including a disposable medicine delivery unit in accordance with the invention.

Referring first to FIG. 1, illustrated is a needleless hypodermic injector assembly 1 including a disposable, single use, medicine delivery unit 3 in accordance with the present invention. Preferably, injector assembly 1 is an APNHI of the same general type described in aforementioned U.S. patent application Ser. No. 08/483,192. The assembly includes a main injector housing 5. The main injector housing contains a cylinder 6 forming an air chamber 7 and a driving piston 8 slidably mounted in chamber 7. As described in detail in application Ser. No. 08/483,192 (which is incorporated by reference), a line 12 is provided for connecting the air chamber with a relatively low pressure source of air 16. An injection actuator 20 is provided for selectively admitting pressurized air from the source into the air chamber to actuate, i.e., drive, driving piston 8 forward in chamber 7. A discharge piston rod 9 is connected to driving piston 8 to move therewith. A compression spring 10 is attached to the driving piston and extends coaxially with discharge piston rod 9 into a passageway 11 of main injector housing 5.

Passageway 11 is configured to removably receive medicine delivery unit 3. Spring 10 has a disk-shaped platform 13 attached at its distal end. Platform 13 has an axially centered bore allowing free travel of discharge piston rod 10 therethrough. A distal side of platform 13 provides a surface which abuts with a proximal end of medicine delivery unit 3, when unit 3 is fully inserted into passageway 11. When delivery unit 3 is removed, platform 13 engages an annular ledge 14. In this manner, spring 10 serves continuously to bias the driving piston and attached rod 9 in the proximal direction, moving these elements to the beginning of their strokes. This ensures that the driving piston and attached rod 9 are returned to an injection-ready position immediately after each injection, on evacuation of air chamber 7.

Preferably, the distal side of platform 13 forms part of a bayonet locking device. Lock part 15 forms, together with an opposing internal annular wall (not visible) of housing 5, a channel which receives a pair of wings or shoulder flanges 17 (only one seen in FIG. 1) extending radially from medicine delivery unit 3 adjacent a proximal end thereof. A pair of opposed slots are provided in passageway 11 for allowing insertion of delivery unit 3 with flanges 17 aligned with the slots. Once fully inserted, flanges 17 pass out of the slots at the proximal end of passageway 11. Delivery unit 3 is then rotated (e.g., a quarter turn) to secure the flanges within the channel. A cam surface 18 may be provided on lock part 15. Under the biasing force of spring 10, cam surface 18 serves to index and releasably bind the flanges to/in a proper locked position within the channel.

Other arrangements may be used to lock delivery unit 3 within main injector housing 5. For example, a push-button mechanism could be employed for effecting locking and unlocking of delivery unit 3 without requiring direct hand manipulation of delivery unit 3. This would serve to further reduce the possibility of contamination.

In the illustrated embodiment, and as disclosed in application Ser. No. 08/483,192, a medicine chamber filling mechanism 19, including a medicament-filled vial 22, is also removably attached to main injector housing 5. The mechanism includes a helical slot with detent openings at three positions (insert/remove, fill, fire). Element 24 is a pump button actuated during filling to deliver fluid into delivery unit 3. In the manner described in the aforementioned patent application, mechanism 19 serves to deliver a dose of medicament from vial 22 and into delivery unit 3 through a side-loading fill port (to be described). Alternatively, however, medicine delivery unit 3 may be provided (without a port) as a sealed cartridge pre-filled with medicament.

Figure 2:
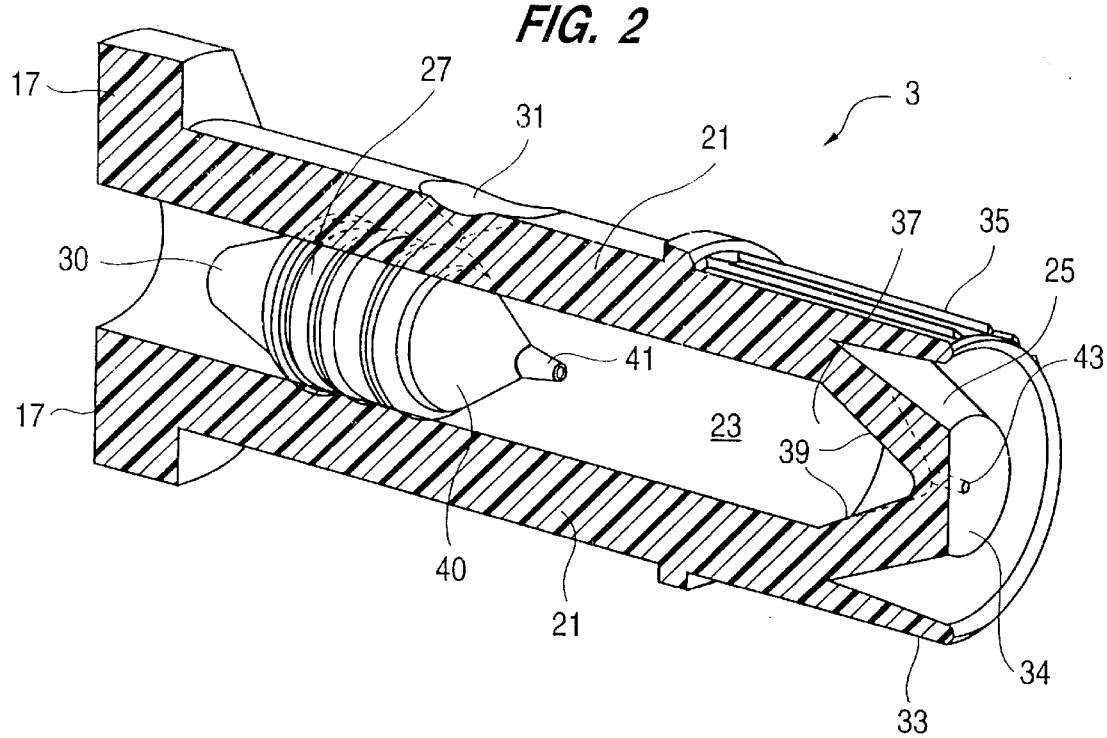
FIG. 2 is a longitudinally sectioned perspective view of the disposable medicine delivery unit, with a piston seal thereof shown in a pre-use position.
Figure 3:
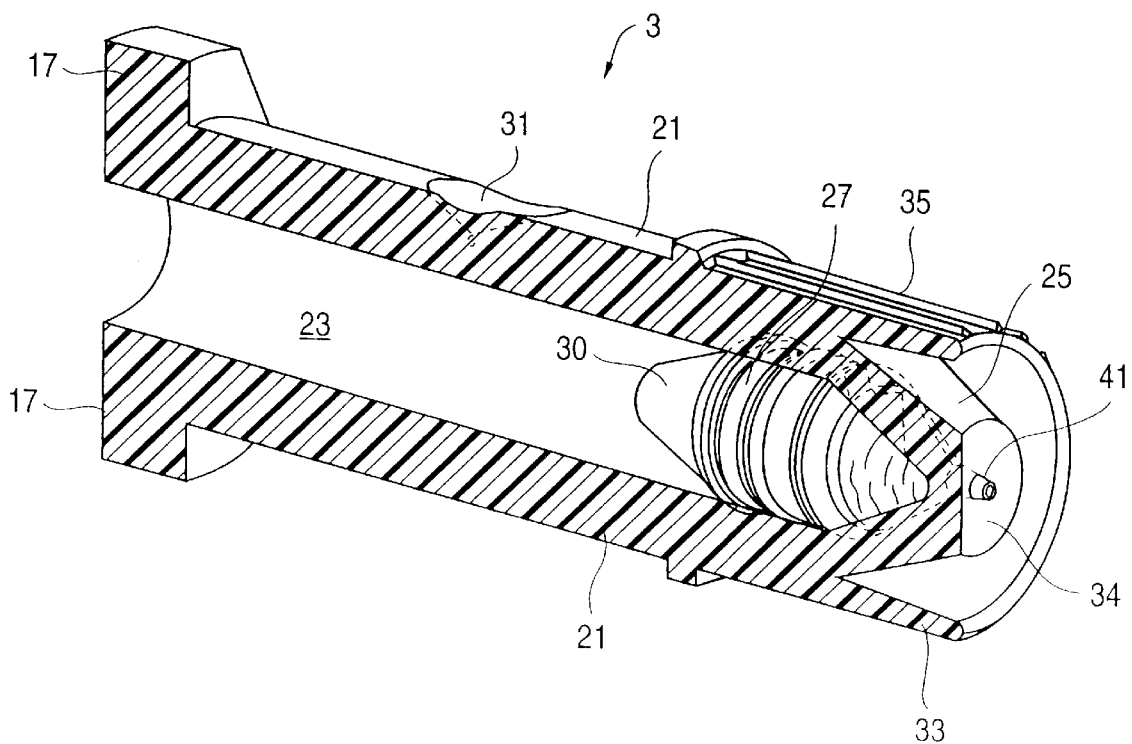
FIG. 3 is a view like FIG. 2 but showing the piston seal in a post-use position at the end of its injection stroke.

Medicine delivery unit 3 is generally cylindrical in shape. As best seen in FIGS. 2–3, unit 3 further comprises generally cylindrical sidewalls 21 defining an elongated medicine chamber 23. A discharge nozzle 25 is connected (preferably molded integrally) with sidewalls 21 at a distal end of chamber 23. A discharge piston seal 27 is slidably mounted for axial movement within chamber 23, from a first position adjacent a proximal end of the chamber to a second position adjacent a distal end of the chamber. As illustrated in FIG. 1, an enlarged cup-like end piece 29 of discharge rod 9 engages a truncated conical proximal end 30 of piston seal 27 to advance it through an injection stroke. (As shown in FIG. 1, seal 27 has been advanced approximately half-way through its injection stroke.) Alternatively, the end of discharge rod 9 could be provided with a truncated conical shape to be engaged by a cup-like proximal end of piston seal 27. In both arrangements, the engagement between discharge rod 9 and piston seal 27 is a push-only engagement, i.e., rod 9 can push, but cannot pull-back, piston seal 27.

Figure 4:
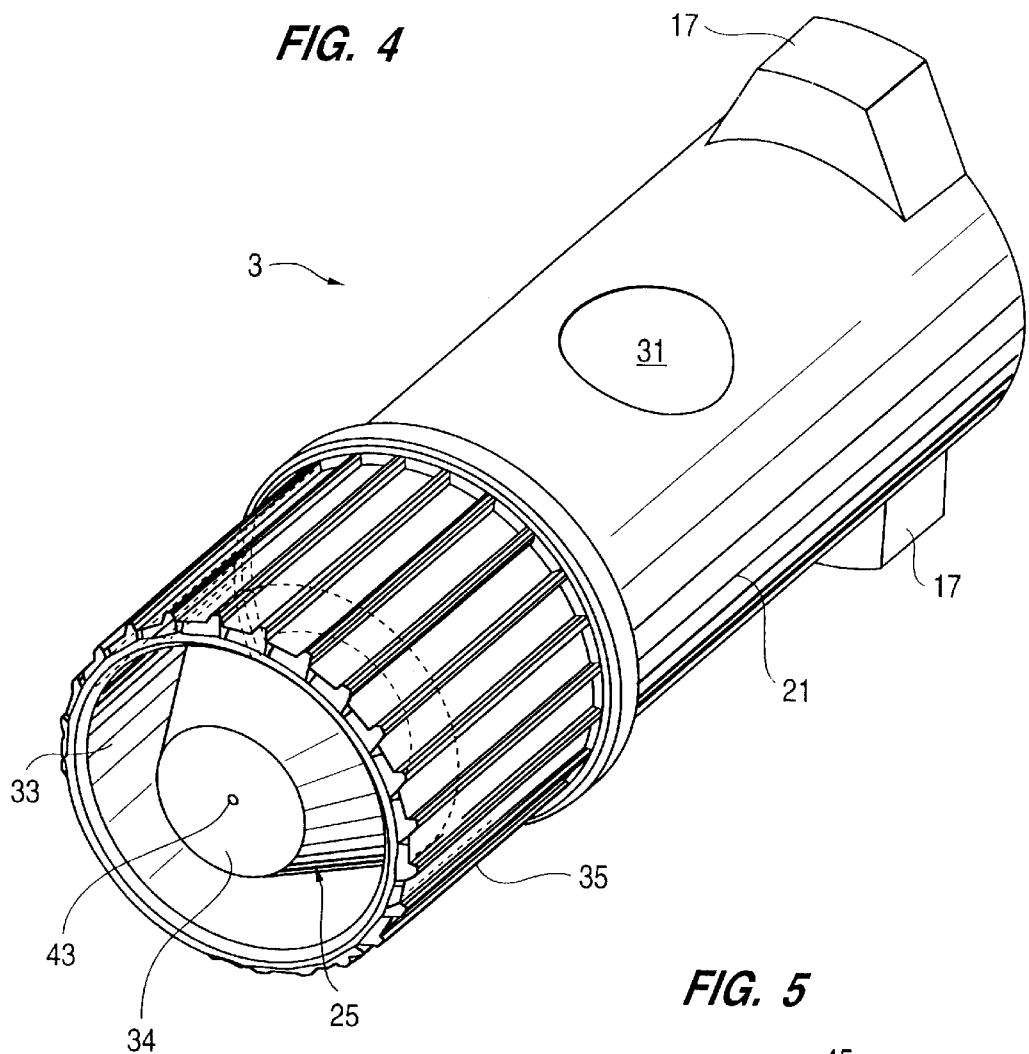
FIG. 4 is a front perspective view of the disposable medicine delivery unit.

FIGS. 2–8 illustrate more clearly the structure and functionality of medicine delivery unit 3. In FIGS. 2–4, it is clearly seen how sidewalls 21 define a side-loading medicine fill port 31. In FIG. 2, piston seal 27 is shown in a pre-injection position adjacent fill port 31. Significantly, by providing a starting position of piston seal 27 adjacent fill port 31, fill port 31 is removed from fluid communication with chamber 23 almost immediately after piston 27 begins its injection stroke. This avoids the need for the problematic check-valves of the prior art (see the Background section). Preferably, fill port 31 is conical and provided with an end orifice of 0.01" diameter.

In order to help with proper initial positioning of piston seal 27 adjacent fill port 31 (e.g., during manufacture), and to reduce compressive loading on seal 27 prior to injection, sidewalls 21 may be formed to provide a chamber diameter (e.g., 0.265") at a proximal side of fill port 31, which is slightly larger than a chamber diameter (e.g., 0.25") directly adjacent and distally of fill port 31. Along with suitable drafts in each chamber section (e.g., 0.5° and 0.25°, respectively), the differential diameters will also facilitate removal of a mold core in an injection molding process.

Sidewalls 21 also preferably define an annular collar 33 which surrounds nozzle 25 and serves to position the nozzle with respect to a skin surface of an injection recipient. As shown, collar 33 lies substantially flush with a distal end surface 34 of nozzle 25, so as to position surface 34 in low-force contact with the skin surface when collar 33 is pressed against the skin surface. Alternatively, as shown in FIG. 9, a collar 33' could be configured to extend slightly beyond nozzle 25, in order to pre-position the nozzle in slightly spaced relation to the skin surface of an injection recipient, e.g., a 4 mm spacing. It has been found desirable to vent the space between the skin surface and nozzle in order to obtain a highly focused jet stream. To this end, collar 33' is equipped with a plurality of (e.g., three) arcuate spacer tabs 36 spaced equally from each other in a circumferential direction to form vent passageways therebetween.

Sidewalls 21 may also define a ribbed or otherwise textured finger grip portion 35 at a distal end of delivery unit 3, in order to facilitate rotation of unit 3 when installing and removing the same in/from main injector housing 5. In the illustrated embodiment, shoulder flanges 17 protrude radially from cylindrical sidewalls 21, adjacent a proximal end thereof Alternatively, the flanges could be provided at a position between the ends of unit 3 in order to reduce the length of sidewalls 21 subjected to tensile stresses generated during an injection stroke.

In accordance with the invention, medicine delivery unit 3 is equipped with at least one (and preferably three) features serving to prevent use of the unit for more than a single injection. First, a distal end region of medicine chamber 23 is provided with a reduced cross-sectional area. As seen in FIG. 3, piston seal 27 is configured relative to the distal end region such that it enters the end region and is securely retained therein (with a greater holding strength than is otherwise present) at the end of its injection stroke. In the illustrated preferred embodiment, a distal end region 37 of chamber 23 is defined by conically tapered interior walls 39 (taper angle $\delta$ of about 65°) of nozzle 25, and piston seal 27 has a mating but slightly larger conical distal end portion 40 which is received within end region 37 with an interference fit. Preferably, entry into distal end region 37 permanently deforms, and thereby destroys, piston seal 27.

The second feature for disabling delivery unit 3 is the previously described push-only engagement between discharge rod 9 and piston seal 27. This prevents use of rod 9 for retracting seal 27.

The third feature for disabling delivery unit 3 is a protruding nub or nipple 41 extending from piston seal distal end portion 40. Nipple 41 is aligned with an injection orifice 43 (best seen in FIGS. 7 and 8) of injection nozzle 25. In a pre-injection condition, orifice 43 preferably has a minimum diameter at its proximal side of 0.005 to 0.006, and conical sidewalls angled with respect to each other by an angle $\alpha$ of about 15°. Upon seal 27 reaching the end of its injection stroke, nipple 41 extends into and permanently deforms orifice 43, thereby destroying its functionality.

Figure 5:
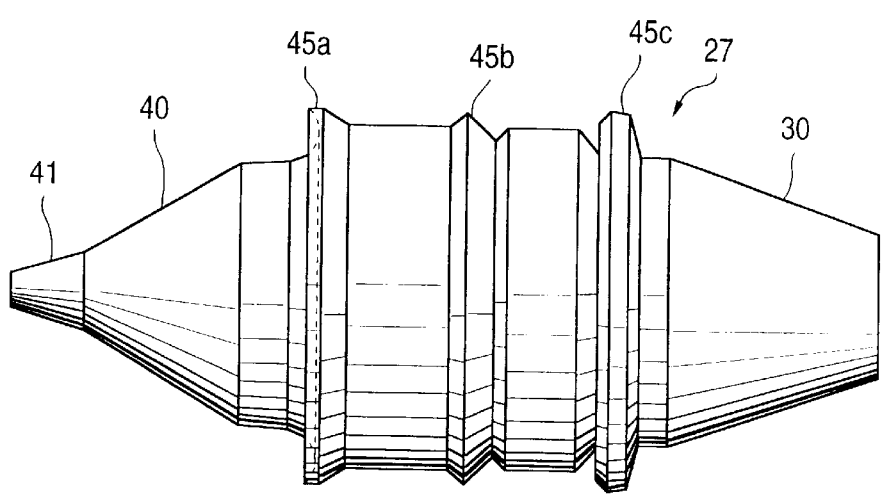
FIG. 5 is a side elevational view of the piston seal.

As best seen in FIG. 5, in order to ensure a good seal that can withstand the high pressures generated during an injection, piston seal 27 comprises a plurality of circumferential fins 45a–c integrally molded with the main seal body. This arrangement eliminates the need for separate dynamic O-ring type seals. In addition, as shown, at least the leading one of the fins 45a is molded with a concave (cupped) cross-sectional shape. This permits the fin(s) to flair (i.e., fold) outwardly slightly during an injection, in order to maximize seal-to-cylinder wall contact.

Preferably, flanges 17, sidewalls 21 and nozzle 25 (i.e., all parts of delivery unit 3 except for piston seal 27) are injection molded as a single piece from medical grade thermoplastic material. The material may be a medical grade semi-rigid engineering polymer, such as polycarbonate. However, for widespread public health applications where cost is critical, these parts are preferably integrally molded of a clear, medical grade, low cost commodity polymer such as impact modified styrene. An example of a material which has been successfully used is K-Resin KR03 from Phillips 66 Company, a modified butadiene styrene. This material is less brittle than unmodified styrene (it has a flexural modulus of 205,000 psi versus a typical styrene modulus of 250,000 psi). This property allows the cylinder (sidewalls 21) to expand elastically during an injection. A more brittle material will tend to fracture during the initial high pressure loads of injection. A material with an even lower modulus may expand too much, allowing "blow-by" of liquid medicament past piston seal 27.

With the use of commodity rather than engineering polymers as aforesaid, it may be necessary to increase sectional thicknesses of the parts in order to obtain the necessary strength. In addition, as aforementioned, it may be desirable to move shoulder flanges 17 to a position between the ends of unit 3 in order to reduce the length of sidewalls 21 subjected to tensile injection stresses.

Particularly with nozzle-skin spaced embodiments of the type shown in FIG. 9, it is critical that nozzle 25 be formed with a high degree of precision. Despite the low Reynolds (approximately Re=1000) flow in the nozzle orifice, turbulence is expected within the free jet. Small imperfections (e.g., 3–5$\mu$) will produce lateral flows that impinge on the main core of the free jet. These lateral flows are also believed to be caused by a large radius (over 0.005") on the inside upstream (proximal) edge of orifice 43. Mixing of these small lateral flows with the main core of the jet causes turbulence. As the turbulent eddies flow out of the orifice, rapid growth of the turbulence occurs due to the adverse Pressure gradient along the free jet. By minimizing the radius of the proximal edge of orifice 43 (creating a sharper edge), and reducing imperfections along the nozzle flow path surfaces, improved jet coherence may be obtained.

As best seen in FIG. 8, a flattened nozzle surface 47 extends perpendicularly to the longitudinal axis of chamber 23 adjacent orifice 43. This, together with small orifice taper angle $\alpha$, provides a sharp (acute) proximal orifice edge. Such a sharp edge is believed to increase coherence of the liquid jet by accelerating laminar fluid flow at the outside of the jet. The sharp edge, along with the taper along the length of the orifice, is also believed to improve jet coherence by reducing contact between the orifice walls and the jet.

The piston seal may be injection molded of any semi-flexible medical-grade polymer such as Delrin (Polyacetal), PVC, or urethane. To maintain low cost and to provide the best auto-destruct characteristics, piston seal 27 is preferably molded of a polyolefin such as Montell Pro-fax SR-857M polypropylene. This material is flexible enough to enable molded sealing fins 45 to conform to the cylinder walls yet rigid enough to withstand injection pressures of 3000 psi. The flexural modulus of SR-857M is 130,000 psi. This characteristic of the preferred material allows piston seal 27 to deform permanently as it enters distal end region 37 at the end of its injection stroke. This material also has a relatively low tensile strength (under 4000 psi) so that it will readily permanently deform if tampered with.

The present invention has been described in terms of preferred and exemplary embodiments thereof. Numerous other embodiments and variations within the scope and spirit of the appended claims will occur to persons of ordinary skill in the art from a review of this disclosure.

We claim:

1. A disposable medicine delivery unit for a needleless hypodermic injector, comprising:

sidewalls defining an elongated medicine chamber;

a releasable lock device connected to said sidewalls for detachably mounting the delivery unit to a main injector housing;

a discharge nozzle connected with said sidewalls at a distal end of said medicine chamber, a distal end region of said medicine chamber adjacent said nozzle having a reduced cross-sectional area; and a discharge piston seal slidably mounted for axial movement within said medicine chamber from a first position adjacent a proximal end of said medicine chamber to a second position within said distal end region of the medicine chamber, said piston seal being configured relative to said distal end region of the medicine chamber such that it enters said end region and is securely retained therein, with a holding strength increased relative to the frictional forces resisting sliding of the piston seal out of said first position, at the end of its injection stroke;

wherein said distal end region of the medicine chamber is defined by conically tapered interior walls of said discharge nozzle, and said piston seal has a mating but slightly larger conical distal end portion for receipt within said distal end region with an interference fit.

2. The disposable medicine delivery unit according to claim 1, wherein said sidewalls further define a medicine fill port adjacent said proximal end of said medicine chamber, said medicine fill port being adapted to be connected to a source of liquid medicament.

3. The disposable medicine delivery unit according to claim 1, wherein said piston seal permanently deforms upon entry into said end region.

4. The disposable medicine delivery unit according to claim 1, wherein said discharge nozzle comprises an injection orifice and said piston seal comprises a protrusion extending from a distal end thereof and aligned with said injection orifice, said protrusion extending into and permanently deforming said injection orifice when said piston seal reaches the end of its injection stroke.

5. The disposable medicine delivery unit according to claim 1, wherein said piston seal comprises at least one circumferential sealing fin which flares outwardly against said sidewalls under pressure generated in said medicine chamber during an injection.

6. The disposable medicine delivery unit according to claim 1, further comprising a collar surrounding said discharge nozzle and serving to position said nozzle with respect to a skin surface of an injection recipient.

7. The disposable medicine delivery unit according to claim 6, wherein said discharge nozzle comprises a distal end surface and said collar lies substantially flush with said distal end surface, so as to position said surface in low force contact with the skin surface when said collar is pressed against the skin surface.

8. The disposable medicine delivery unit according to claim 6, wherein said collar extends slightly beyond a distal end surface of the discharge nozzle, to pre-position the nozzle in slightly spaced relation to said skin surface.

9. The disposable medicine delivery unit according to claim 8, wherein said collar defines a passageway to vent the space between the skin surface and distal end surface of the discharge nozzle.

10. The disposable medicine delivery unit according to claim 8, wherein said discharge nozzle comprises an injection orifice having an acute proximal edge.

11. The disposable medicine delivery unit according to claim 10, wherein said injection orifice tapers slightly in a proximal direction from said distal end surface.

12. The disposable medicine delivery unit according to claim 1, wherein said releasable lock device comprises a shoulder flange forming part of a bayonet-type releasable lock device.

13. The disposable medicine delivery unit according to claim 1, wherein said releasable lock device, said sidewalls and said discharge nozzle are molded as a single piece from medical grade commodity polymer.

14. The disposable medicine delivery unit according to claim 13, wherein said medical grade commodity polymer is a medical grade modified styrene.

15. The disposable medicine delivery unit according to claim 14, wherein said modified styrene is substantially clear.

16. The disposable medicine delivery unit according to claim 14, wherein said medical grade commodity polymer is a butadiene styrene polymer.

17. The disposable medicine delivery unit according to claim 13, wherein said commodity polymer has a flexural modulus of approximately 205,000 psi.

18. The disposable medicine delivery unit according to claim 1, wherein said piston seal is injection molded as a single piece of semi-flexible medical grade polymer.

19. The disposable medicine delivery unit according to claim 18, wherein said medical grade polymer is a polyolefin.

20. The disposable medicine delivery unit according to claim 18, wherein said medical grade polymer has a flexural modulus of approximately 130,000 psi.

21. The disposable medicine delivery unit according to claim 18, wherein said medical grade polymer has a tensile strength of less than 4000 psi.

22. The disposable medicine delivery unit according to claim 1, said disposable medicine delivery unit comprising a sealed cartridge pre-filled with medicament.

23. A needleless hypodermic injector assembly, comprising:
a main injector housing containing a reciprocable driving member and a discharge rod attached to said driving member; and
a disposable medicine delivery unit, said delivery unit including:
sidewalls defining an elongated medicine chamber and a medicine fill port adjacent a proximal end of said medicine chamber, said fill port being adapted to be connected to a source of liquid medicament;
a releasable lock device connected to said sidewalls and detachably mounting the delivery unit to said main injector housing;
a discharge nozzle connected with said sidewalls at a distal end of said medicine chamber; and a discharge piston seal slidably mounted for axial movement within said medicine chamber from a first proximal position adjacent said medicine fill port to a second distal position within an end region of the medicine chamber adjacent said discharge nozzle, said piston seal having a proximal end surface engageable in a push-only relation with a distal end of said discharge rod when said delivery unit is mounted in the main injector housing;
wherein said end region of the medicine chamber has a reduced cross-sectional area and said piston seal is configured relative to said end region such that it enters said end region and is securely retained therein, with a holding strength increased relative to the frictional forces resisting sliding of the piston seal out of said first proximal position, at the end of its injection stroke.

24. The needleless hypodermic injector assembly according to claim 23, wherein said distal end region of the medicine chamber is defined by conically tapered interior walls of said discharge nozzle, and said piston seal has a mating by slightly larger conical distal end portion for receipt within said end region with an interference fit.

25. The injector assembly according to claim 23, wherein said main injector housing further contains:
an air chamber, said driving member comprising a driving piston slidably mounted in said air chamber;
a line extending from said air chamber for connecting the air chamber with a source of pressurized air, and an injection actuator operatively connected to said line for selectively admitting pressurized air from said source into said air chamber to actuate the driving piston.

26. The injector assembly according to claim 25, said main injector housing further comprising a compression spring and a passageway configured to receive said medicine delivery unit, said spring being attached to said driving piston and extending coaxially with said discharge rod into said passageway, said compression spring having a platform attached at its distal end, said platform further having an axial bore for free travel of said discharge rod therethrough, whereby when said delivery unit is mounted in said main housing, said compression spring biases said driving piston, and the attached discharge rod, in the proximal direction.

27. A disposable medicine delivery unit for a needleless hypodermic injector, comprising:
sidewalls defining an elongated medicine chamber;
a releasable lock device connected to said sidewalls for detachably mounting the delivery unit to a main injector housing;
a discharge nozzle connected with said sidewalls at a distal end of said chamber, a distal end region of said chamber adjacent said nozzle having a reduced cross-sectional area; and
a discharge piston seal slidably mounted for axial movement within said chamber from a first position adjacent a proximal end of said chamber to a second position within said distal end region of the chamber, said discharge nozzle comprising an injection orifice and said piston seal comprising a protrusion extending from a distal end thereof and aligned with said injection orifice, said protrusion extending into and permanently deforming said injection orifice when said piston seal reaches the end of its injection stroke.

28. A disposable medicine delivery unit for a needleless hypodermic injector, comprising:
sidewalls defining an elongated medicine chamber;
a releasable lock device connected to said sidewalls for detachably mounting the delivery unit to a main injector housing; and a discharge nozzle connected with said sidewalls at a distal end of said chamber, said discharge nozzle having an injection orifice with an acute proximal edge.

29. A disposable medicine delivery unit according to claim 28, wherein said nozzle comprises a distal end surface and said injection orifice tapers slightly in a proximal direction from said distal end surface.

30. A disposable medicine delivery unit for a needleless hypodermic injector, comprising:

sidewalls defining an elongated medicine chamber;

a releasable lock device connected to said sidewalls for detachably mounting the delivery unit to a main injector housing;

a discharge nozzle connected with said sidewalls at a distal end of said medicine chamber, a distal end region of said medicine chamber adjacent said nozzle having a reduced cross-sectional area; and a discharge piston seal slidably mounted for axial movement within said medicine chamber from a first position adjacent a proximal end of said medicine chamber to a second position within said distal end region of the medicine chamber, said piston seal being configured relative to said distal end region of the medicine chamber such that it enters said end region and is securely retained therein, with a holding strength increased relative to the frictional forces resisting sliding of the piston seal out of said first position, at the end of its injection stroke;

wherein said sidewalls further define a medicine fill port adjacent said proximal end of said medicine chamber, said medicine fill port being adapted to be connected to a source of liquid medicament.

31. A disposable medicine delivery unit for a needleless hypodermic injector, comprising:

sidewalls defining an elongated medicine chamber;

a releasable lock device connected to said sidewalls for detachably mounting the delivery unit to a main injector housing;

a discharge nozzle connected with said sidewalls at a distal end of said medicine chamber, a distal end region of said medicine chamber adjacent said nozzle having a reduced cross-sectional area; and a discharge piston seal slidably mounted for axial movement within said medicine chamber from a first position adjacent a proximal end of said medicine chamber to a second position within said distal end region of the medicine chamber, said piston seal being configured relative to said distal end region of the medicine chamber such that it enters said end region and is securely retained therein, with a holding strength increased relative to the frictional forces resisting sliding of the piston seal out of said first position, at the end of its injection stroke;

wherein said piston seal permanently deforms upon entry into said region.

32. A disposable medicine delivery unit for a needleless hypodermic injector, comprising:

sidewalls defining an elongated medicine chamber;

a releasable lock device connected to said sidewalls for detachably mounting the delivery unit to a main injector housing;

a discharge nozzle connected with said sidewalls at a distal end of said medicine chamber, a distal end region of said medicine chamber adjacent said nozzle having a reduced cross-sectional area; and a discharge piston seal slidably mounted for axial movement within said medicine chamber from a first position adjacent a proximal end of said medicine chamber to a second position within said distal end region of the medicine chamber, said piston seal being configured relative to said distal end region of the medicine chamber such that it enters said end region and is securely retained therein, with a holding strength increased relative to the frictional forces resisting sliding of the piston seal out of said first position, at the end of its injection stroke;

wherein said discharge nozzle comprises an injection orifice and said piston seal comprises a protrusion extending from a distal end thereof and aligned with said injection orifice, said protrusion extending into and permanently deforming said injection orifice when said piston seal reaches the end of its injection stroke.

33. A disposable medicine delivery unit for a needleless hypodermic injector, comprising:

sidewalls defining an elongated medicine chamber;

a releasable lock device connected to said sidewalls for detachably mounting the delivery unit to a main injector housing;

a discharge nozzle connected with said sidewalls at a distal end of said medicine chamber, a distal end region of said medicine chamber adjacent said nozzle having a reduced cross-sectional area;

a discharge piston seal slidably mounted for axial movement within said medicine chamber from a first position adjacent a proximal end of said medicine chamber to a second position within said distal end region of the medicine chamber, said piston seal being configured relative to said distal end region of the medicine chamber such that it enters said end region and is securely retained therein, with a holding strength increased relative to the frictional forces resisting sliding of the piston seal out of said first position, at the end of its injection stroke; and a collar surrounding said discharge nozzle and serving to position said discharge nozzle with respect to a skin surface of an injection recipient, wherein said collar extends slightly beyond a distal end surface of the discharge nozzle, to pre-position the discharge nozzle in slightly spaced relation to said skin surface, and said discharge nozzle comprises an injection orifice having an acute proximal edge.

34. The disposable medicine delivery unit according to claim 33, wherein said injection orifice tapers slightly in a proximal direction from said distal end surface.

* * * * *